United States Patent [19]

Lauks et al.

[11] Patent Number: 4,629,424
[45] Date of Patent: Dec. 16, 1986

[54] INTRAORAL AMBIENT SENSING DEVICE

[75] Inventors: Imants R. Lauks, Sewell; Samuel L. Yankell, Moorestown, both of N.J.

[73] Assignee: Integrated Ionics, Inc., Princeton, N.J.

[21] Appl. No.: 645,940

[22] Filed: Aug. 30, 1984

[51] Int. Cl.$^4$ .............................................. A61C 3/00
[52] U.S. Cl. ...................................... 433/6; 433/32; 128/777; 455/100
[58] Field of Search ................... 433/6, 32, 167; 128/777, 776, 787; 455/100

[56] References Cited

U.S. PATENT DOCUMENTS

| | | | |
|---|---|---|---|
| 2,161,169 | 6/1939 | Jefferis | 433/167 |
| 3,170,993 | 2/1965 | Puharich et al. | 433/32 |
| 3,209,081 | 9/1965 | Ducote et al. | 455/100 |
| 3,253,588 | 5/1966 | Vuilleumier et al. | 455/100 |
| 3,277,892 | 10/1966 | Tepper | 433/6 |
| 3,297,021 | 1/1967 | Davis et al. | 128/777 |
| 3,374,787 | 3/1968 | Hatke | 455/100 |
| 3,958,560 | 5/1976 | March | 455/100 |
| 4,153,060 | 5/1979 | Korostoff et al. | 433/32 |
| 4,255,138 | 3/1981 | Frohn | 433/6 |
| 4,334,542 | 6/1982 | Takinishi et al. | 128/787 |

OTHER PUBLICATIONS

Popular Mechanics, Jan. 71, pp. 94 and 95, "Tooth Transmitter".
Nature, Apr. 1961, pp. 90 and 91, "Determination of Physiological Rhythms of Unrestrained Animals by Radio Telemetry".

Primary Examiner—John J. Wilson
Attorney, Agent, or Firm—Pennie & Edmonds

[57] ABSTRACT

A device is disclosed for intraoral ambient sensing. In this embodiment, the device comprises a removable oral (Hawley) appliance containing a number of chemically sensitive electrodes and a common reference electrode at the chemical sensing sites and a telemetry unit plus power pack for signal transmission. This device may also be used to monitor non-chemical parameters, notably pressure, temperature, and flow. In this embodiment, the removable oral (Hawley) appliance contains a number of sensors to monitor the parameter of interest. For example, a pressure sensor configured as an artificial uvula and mounted to the oral (Hawley) appliance emulates actual uvula pressure events. To monitor chewing events, a pressure sensor is mounted to the oral (Hawley) appliance in such a manner that it is optimally located at an open bite location of the mouth. In either embodiment, a telemetry unit mounted to the oral (Hawley) appliance transmits the intraoral ambient information as radio frequency signal bursts. A remotely located receiver circuit receives the radio signals which are broadcast and recovers the information encoded in them.

16 Claims, 11 Drawing Figures

- Stainless Steel 7
- Acrylic 2
- Antenna 6
- Telemetry Circuit 4
- $Ag_2O$ Dry Cell 5 pH Electrode

- Platinel
- Sirof

Reference Electrode

- 0.1M KCl Acrylamide Gel
- Ag/AgCl Contact to Oral Fluids

INTRAORAL AMBIENT SENSING DEVICE

CROSS REFERENCE TO RELATED APPLICATIONS

Related applications are "Ambient Sensing Extended Gate Transistors", Ser. No. 572,182; "Integrated Arrays of Ambient Sensing Devices", Ser. No. 572,199; "Integrated Ambient Sensing Devices and Method of Manufacture", Ser. No. 572,185; "Method of Calibrating Amorphous Metal Oxide Electrodes," Ser. No. 572,200, now U.S. Pat. No. 4,551,209; and "Ambient Sensing Devices Using Polyimide", Ser. No. 572,213, filed Jan. 19, 1982, and "Amorphous Metal Oxide Electrodes," Ser. No. 441,902, filed Nov. 15, 1982, which are incorporated herein by reference.

BACKGROUND OF THE INVENTION

The present invention relates to measurement devices which are to be mounted within the oral cavity. Such measurement devices may be sensitive to the concentration of one or more ionic species or to non-chemical parameters such as pressure, temperature, and flow. In accordance with certain preferred embodiments, sensors are provided for telemetric monitoring of intraoral parametric changes at multiple intraoral sites.

Numerous types and configurations of ion sensitive electrodes are known to those skilled in the art. See, for example, the above-referenced U.S. patent application for "Amorphous Metal Oxide Electrodes", Ser. No. 441,902. As discussed in that application, prior art electrodes include discrete elements such as glass electrodes and metal oxide electrodes. As disclosed in application Ser. No. 441,902, an especially useful electrode is one made of an amorphous oxide of a metal selected from the platinum or rhenium groups of metals. Preferably such electrodes are formed by applying such amorphous oxide as the gate material in a field effect transistor. The resulting ion sensitive field effect transistor (ISFET) is highly effective for the detection and measurement of ionic species, especially pH.

One area of considerable research interest involving pH measurements is the measurement of intraoral pH and especially plaque pH. It has long been known that the acidic fermentation products produced by plaque microorganisms in the presence of sugar and carbohydrates are strongly associated with dental caries. See, for example, Stephan, R.M., "Changes in hydrogen-ion concentration on tooth surfaces and in carious lesions", *J. Amer. Dental Assn.*, vol. 27, pages 718–723 (1940); Straffors, A., "Investigations into the bacterial chemistry of dental plaque", *Odont. Tidsler.* vol. 58, pages 155–341 (1950). Because of this known importance of plaque pH, measurement of plaque pH is now widely accepted as a method of evaluating the effect of carbohydrates on oral health. Yankell, S. L., et al., "In vitro Testing of a New System for Monitoring pH at Multiple Sites", *Caries Res.*, vol. 17, pages 439–443 (1983) which is incorporated herein by reference.

There are, however, considerable difficulties in the measurement of plaque pH and other intraoral parameters of interest using prior art devices. Prior art devices were frequently too large, difficult or objectionable to mount within the patient's mouth and limited in their capacity to monitor events of interest. Yankell, S. L., et al., "Development of Telemetric Intraoral Chemical Sensing Systems", Annual Conference on Engineering in Medicine and Biology (1982). For example, most successful in vivo pH sensing systems to date place the microelectrodes in prosthetic teeth, providing a surface for plaque deposition at an interproximal site adjacent to a natural tooth (Schactele and Jensen, 1982; Firestone, 1982). The same site can be noninvasively observed over time and during various oral functions such as rinsing and chewing. There are, however, several shortcomings in these approaches. Constraints are imposed on subject selection due to the requirements for teeth that are missing or in need of being crowned. With these current systems using glass electrodes, the response time is relatively slow; the high electrode impedance leads to noise problems and the large size of even the smallest glass microelectrode precludes efficient monitoring of multiple sites and makes nonintrusive monitoring at interproximal sites impossible. While the above-referenced paper by Yankell describes a proposed system that avoids many of these problems, it has been found that while it works satisfactorily in vitro it does not perform satisfactorily in vivo.

SUMMARY OF THE INVENTION

We have devised a new system for in vivo monitoring of oral biochemistry. In an illustrative embodiment of our invention, the system comprises a removable oral (Hawley) appliance containing a number of chemically sensitive electrodes at the chemical sensing sites and a common reference electrode and a telemetry unit plus power pack for signal transmission. To assure satisfactory performance of the device, the sensors, sensor leads and all electronics are hermetically sealed.

In another embodiment of the present invention, we have devised a new system for in vivo monitoring of non-chemical parameters, notably pressure, temperature, and flow. Measurement of these parameters is of interest in ongoing medical research to diagnose, treat or prevent disease. For example, the number of swallows may be related to obesity. In accordance with this aspect of our invention, the system comprises a removable oral (Hawley) appliance containing a number of pressure, temperature, and/or flow transducers at each oral sensing location and a telemetry unit plus power pack for signal transmission. Again all sensors, leads and electronics are hermetically sealed for in vivo use.

The Hawley appliance used in both aspects of the present invention is a retainer structure commonly used in orthodontics such as for the regulation of teeth development in children.

The chemically sensitive electrodes of the biochemistry monitoring system depend on the chemical or ion activity to be monitored. For example, intraoral measurement of pH could advantageously use sputtered iridium oxide electrodes as the chemically sensitive electrode. In this case, the reference electrode could be formed using an acrylamide gel salt bridge contacting Ag/AgCl. All sensors are advantageously mounted to the Hawley appliance for intraoral sensing purposes.

The non-chemical sensing transducers also depend on the parameter to be monitored. For example, pressure measurement could advantageously use the PVF2 (polyvinylidene fluoride) piezoelectric polymer as the pressure transducer. Being highly piezoelectric, this polymer generates large electrical signals whenever force is applied to the sensor. In addition, the polymer exhibits a large pyroelectric effect which can be utilized to obtain additional information about local temperature. As a high impedance voltage source, the polymer is compatible with radio telemetry circuitry.

When used to monitor swallowing events, the pressure sensor can be advantageously configured as an "artificial uvula" to emulate actual uvula pressure events. When used to monitor chewing events, the pressure sensor can be located in an anterion placement of the palate to record tongue movement during chewing, or optimally at an open bite location of the mouth where the maxillary and mandibula are not in contact when the mouth is closed. In this latter configuration, the sensor is held in place by a cantilever hinged at the lingual side of the acrylic of the Hawley appliance near the open bite location of the mouth and terminating at the open bite location of the mouth. In this manner, the apparatus monitors only chewing in a mouth containing food since chews in the absence of food do not impart force upon the sensor.

The telemetry unit for signal transmission invention is formed using either discrete components or an integrated circuit and both the telemetry unit and a power pack are mounted in the Hawley removable dental appliance to permit signal transmission of intraoral activities to a remote location without the use of electrical wires. Thus, tethering of a test subject to remote recording devices is avoided. By removing the restrictions imposed by wires on the movement of the subject, the resulting data more accurately reflect the intraoral activities generally occuring during a subject's ordinary activities. The radio telemetry unit receives signals from the intraoral monitoring sensors and after modulating the signal, broadcasts the signal upon a radio frequency carrier. A remotely located receiver and demodulator receives the broadcast signal and demodulates the same to obtain the converted intraoral signal. In a simpler version of the present invention, signals can be telemetered by wires coming out of the mouth. This system is appropriate for non-ambulatory studies when the patient can be connected by wire to signal acquisition equipment.

BRIEF DESCRIPTION OF DRAWINGS

These and other objects, features and advantages of the invention will be more-readily apparent from the following description of the preferred embodiments of the invention in which:

FIGS. 2-1 through 2-5 are schematic illustrations of the modifications to the Hawley appliance to mount ion sensitive electrodes and a radio telemetry unit in accordance with this invention;

FIG. 3 is a schematic of a telemetric intraoral sensing device which monitors forces at multiple sites;

FIG. 4 is a schematic of a telemetry circuit for radio telemetry of the electrical signals from sensors which are attached to the Hawley appliance;

FIG. 5 is a schematic of a second embodiment of a telemetry circuit for radio telemetry of the electrical signals from sensors which are attached to the Hawley appliance;

PREFERRED EMBODIMENTS

Figure 1:
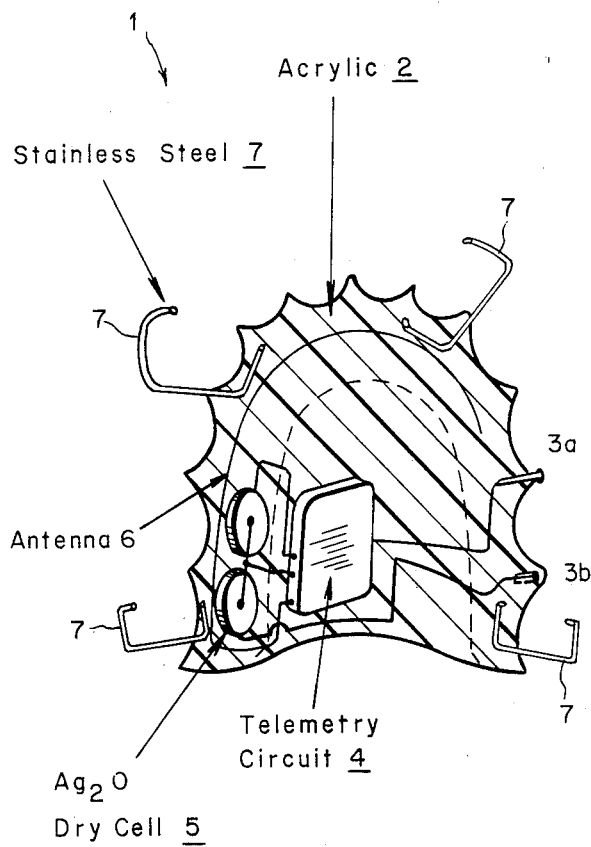
FIG. 1 is a schematic illustration of a telemetric intraoral sensing device of the present invention.

As shown in FIG. 1, a telemetric intraoral sensing device 1 comprises Hawley appliance 2, sensors 3a, 3b, telemetry circuit 4, power pack 5, antenna 6, and dental engaging members 7. The chemical sensor 3a reference electrode 3b, telemetry circuit 4, power pack 5 and antenna 6 are all mounted on the Hawley appliance and dental engaging members 7 secure the Hawley appliance to the patient's teeth.

Hawley appliance 2 is a retainer structure commonly used in orthodontics such as for the retention of the position of teeth. The appliance is formed by taking an impression of the teeth which is to accomodate the sensors and appliance. Dental stone is then poured into the impression and the resulting cast trimmed and all artificial bubbles or imperfections removed. Finally, the stone cast is lubricated with a separating medium which prevents the acrylic base of the Hawley appliance from sticking to the stone. The acrylic base is added via a liquid drop and powder which results in a well adapted, custom fitted acrylic base which will cover the hard palate. In general, a smooth surface facilitates attachment to the apparatus of sensor 3a and reference electrode 3b, telemetry circuit 4, power pack 5, antenna 6, and dental engaging members 7.

Sensor 3a is an ion sensitive electrode which at one surface is capable of undergoing a reversible electrochemical reaction or redox reaction with an ionic species to be detected and to produce an output electric signal proportional to the logarithm of concentration of the ion. In the preferred embodiment, a sputtered iridium oxide electrode is used as the chemically sensitive electrode for monitoring pH while a polyvinyl chloride membrane electrode is used as the electrode for monitoring calcium. Enlargement 8 shows the electrode and its hardwire connection which serves as an electrical signal path from the electrode to the telemetry circuit 4. The electrode is joined to the hardwire with solder. As shown in enlargement 8, the chemically sensitive iridium oxide surface of sensor 3a is oriented toward the interproximal side of the appliance for pH monitoring in the interproximal location Enlargement 9 shows an enlargement of electrode 3b, a reference electrode 9a containing acrylamide gel 9b. One end of the electrode is in contact with oral cavity fluids. At the other end, the reference electrode is soldered to hardwire which serves as an electrical signal path to the telemetry circuit 4. Further details concerning the construction of sensor 3a and electrode 3b are set forth in conjunction with FIGS. 2-2 through 2-4.

Telemetry circuit 4 is a radio telemetry circuit that broadcasts a modulated radio frequency carrier signal to a remote location. In one preferred embodiment, pulse-amplitude and pulse width modulation are used to encode signals from the ion sensitive electrodes into a form suitable for broadcasting. Other modulating techniques well known to those working in the field, such as frequency modulation or pulse position modulation, are also possible.

Power pack 5 generates electrical energy for powering telemetry circuit 4 and antenna 6. As detailed below, the size and location of the power pack facilitates incorporation into Hawley appliance 2 without obstructing sensor operation or creating discomfort to the subject wearing the Hawley appliance.

Antenna 6 is an antenna element which can broadcast radio frequency bursts from telemetry circuit 4 to a remote location.

Engaging members 7 are stainless steel wires ranging from 0.28 to 0.36 inches in diameter which are adapted to fasten the Hawley appliance to two posterior teeth and two anterior teeth.

To use the sensing device, the Hawley device should be fitted to the patient's teeth and the sensor 3a positioned on the Hawley device so as to monitor the parameters of interest. The reference electrode 3b should be positioned in any location in contact with oral fluid. The Hawley device should then be placed in the oral cavity of the patient and mounted on the teeth. Once mounted, sensor 3a continuously monitors the parameter to which it is sensitive and generates an electrical signal (with respect to reference 3b) proportional thereto. As discussed below, this signal is then broadcast by telemetry circuit 4 and antenna 6 to a remote location at which the broadcast signal is received and demodulated to retrieve the intraoral information. Remotely located information recording devices such as display recorders and computer storage illustratively are used to provide accurate real time and batch time study of the patient's intraoral activities. Such data are useful, for example, in the diagnosis and treatment of disease.

Figures 1, 2:
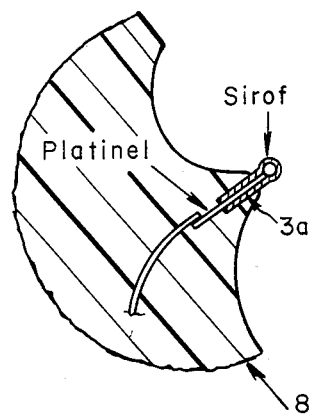

Fabrication of the Hawley appliance has been described above. FIG. 2 depicts a method for modifying this device to mount ion sensitive electrodes and a radio telemetry unit. The Hawley appliance 2 is modified as shown in FIG. 2-1. This modication involves molding thicker acrylic on the lingual side of the appliance at each point where an interproximal sensor is to be placed. Once hardened the Hawley appliance 2 is removed from the stone cast model and is further modified as shown in FIGS. 2-2 through 2-5.

As shown in FIG. 2-2, at the point where a sensor is to be located, a hole is drilled between the lingual side and the interproximal side of the acrylic 19 of the appliance just large enough to accomodate the sensor. The sensor is then placed in the drilled hole with the sensor oriented toward the intraoral activity to be monitored. For example, FIG. 2-2 shows a sputtered iridium oxide pH electrode 3a on nylon. The electrode shaft is electrically insulated with silicone rubber paint 23 which covers the shaft and thereby prevents electrochemical reactions between the shaft and the surrounding environment. As shown in FIG. 2-2, the chemically sensitive surface of the electrode is oriented toward the interproximal side of the appliance for pH monitoring in interproximal locations. Alternatively, the chemically sensitive surface of the electrode could be oriented toward the oral cavity for pH monitoring of intraoral saliva.

Figures 1, 2, 3:
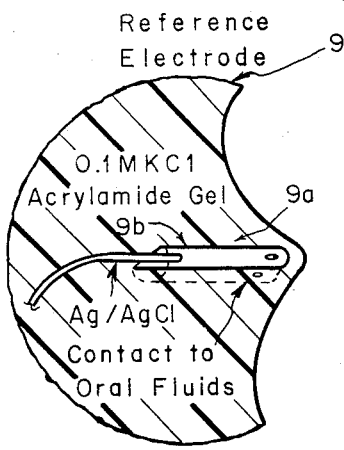

Referring now to FIG. 2-3, once placed in the hole, the sputtered iridium oxide electrode is then electrically connected to a wire 25 using Ag paint 24. The wire 25 is electrically insulated beforehand with a plastic case 26. Both the electrode and the wire are then affixed to the acrylic 21 of the Hawley appliance with silicone rubber 27. This rubber also provides additional electrical insulation to both the electrode shaft and the connecting wire. No rubber covers the sensing surface of the electrode to permit electrochemical reactions between this surface and the environment. Finally, the external surface of the rubber 27 is coated with epoxy 28 to prevent moisture from migrating to both the electrode and the wire Electrodes for other ions such as calcium, fluoride, phosphate and so on can be mounted in a similar fashion. It should be emphasized, that it is important to provide hermetic seals for all sensors, sensor leads and other electronics to ensure satisfactory performance in vivo.

Figures 1, 2:
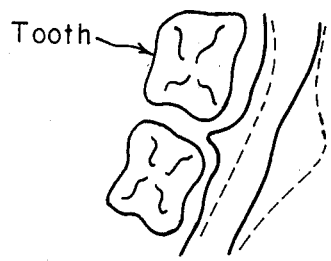
Figure 2:
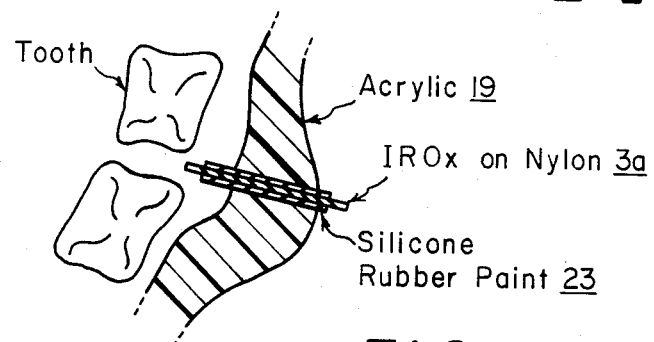
Figures 2, 3:
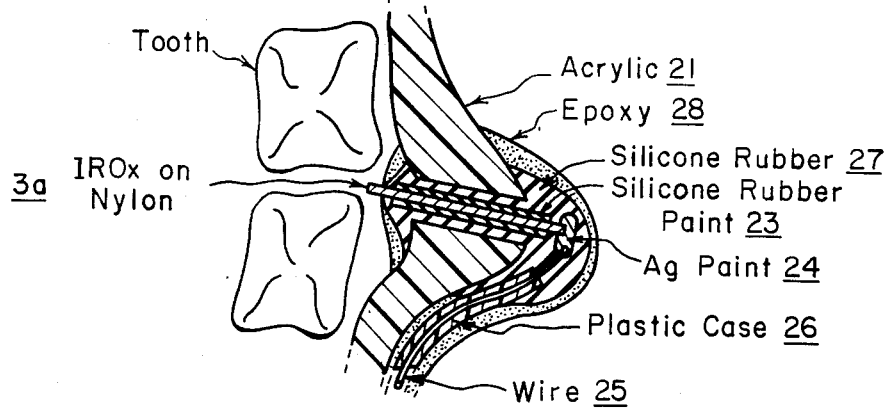
Figures 2, 3, 4:
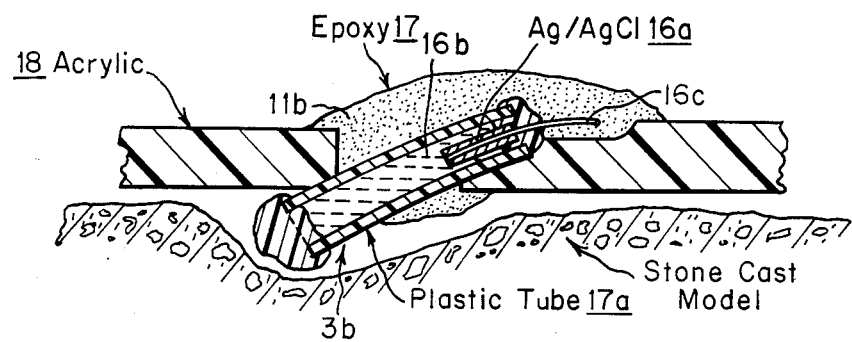

As shown in FIG. 2-4, a reference electrode is also mounted to the Hawley appliance. This electrode comprises an electrode surface 16a, 0.1M KCl acrylamide gel 16b, and wire 16C. The electrode is fabricated by first loading, 0.1M KCl acrylamide gel 16b into plastic tube 17a. Both ends of the tube are sealed. The chemically sensitive surface 16a of the electrode is the silver chloride (Ag/AgCl) coated end of the wire 16c which is inserted into the gel. The wire enters the gel through the sealant on the lingual end of the electrode which sealant also holds the wire in a fixed position in the gel. The opposite end of the wire 16c is connected to the telemetry circuit 4 shown in FIG. 1. Plastic tube 17a is inserted through a previously formed hole in the acrylic of the Hawley appliance and affixed to it with epoxy. Prior to insertion of the appliance in the subject's mouth, plastic tube 17a is cut flush with the surface of the acrylic, so that gel 16b comes into contact with the subject's oral fluid on the palatal side of the appliance. The purpose of the acrylamide gel salt-bridge is to provide electrical connection to the oral fluid so as to complete the circuit (consisting of sensor 3a, oral fluid and reference electrode 3B), but not allow the Ag/AgCl to be exposed to a variable chemical environment thus ensuring constancy of electrode potential of reference electrode 3b.

Referring now to FIG. 2-5, acrylic is then removed from the lingual side of the Hawley appliance to form channels for placement of telemetry circuit 4, power pack 5, and antenna 6. Telemetry circuit 4, power pack 5 and antenna 6 are then positioned on Hawley appliance 2 after which they are electrically interconnected as shown in FIG. 1. Epoxy 13 mounts these electrical elements to the Hawley appliance and also electrically isolates these elements from the environment.

Alternatively, as also shown in FIG. 2-5, a wire connection, instead of a telemetric connection, can be provided to the sensor and reference electrode by wires 14 which are electrically insulated by plastic case 15.

FIG. 3 shows a second preferred embodiment of a telemetric intraoral sensing device 80 which monitors forces at multiple sites. Device 80 comprises Hawley appliance 81, pressure sensor 84 for monitoring swallow forces, pressure sensors 87a and 87b for monitoring chew forces, telemetric circuit 91, power pack 92, antenna device 90, and dental engaging members 93.

Hawley appliance 81, telemetry circuit 91, antenna device 90, power pack 92, and dental engaging members 93 operate in the manner and scope as hereinabove described. Pressure sensor 84 which is used for monitoring swallow forces can be any conventional pressure sensor which generates an electrical signal whenever a force is applied to the sensor. In the preferred embodiment, a piezoelectric force transducer 84 containing PVF2 piezoelectric polymer is used as the pressure transducer element. Being highly piezoelectric, the polymer generates large electrical signals whenever force is applied to the sensor. In addition, the polymer exhibits a large pyroelectric effect which can be utilized to obtain temperature information. As a high impedance voltage source, the polymer is advantageously compatible with radio telemetric circuitry. Also, because the polymer is readily obtainable and inexpensive, it minimizes procurement delays and is cost-effective.

Piezoelectric force transducer 84 is held near the uvula by a cantilever 83 or some other means of elevating it above the plane of the palate. The transducer is attached to one end of the cantilever. The other end of the cantilever is bent to form a tab 82 that is fixed by epoxy to the Hawley appliance. Because the transducer is located near the uvula, the transducer advantageously emulates actual uvula pressure events.

Pressure sensor 87a is used for monitoring chew forces. It is a piezoelectric force transducer which is similar in operation to the pressure sensor previously described with reference to monitoring swallow events. To monitor chewing events, the pressure sensor 87a is located at an open bite location 87c of the mouth where the maxillary and mandibula are not in contact when the mouth is closed. The sensor is held in place by a cantilever 88 comprising a material having properties that meet the requirements of the desired intraoral sensing test plan. The sensor is attached to one end of the cantilever. The other end of the cantilever is bent to form a tab 89 which is affixed by epoxy to the Hawley appliance. By placing the chew sensor in this configuration, the sensor 87 monitors only chewing in a mouth containing food since chews in the absence of food do not impart force upon the sensors. Alternatively, the sensor may be located at site 87b at which location chewing is monitored by pressure of the tongue on the sensor.

FIG. 4 depicts details of an illustrative embodiment of a telemetry circuit for radio telemetry of the electrical signals from seven sensors which are attached to the Hawley appliance. Circuit 100 comprises signal conditioning circuits 101, a multiplexer circuit 102, a voltage to pulse width modulating circuit 103, a radio transmitting circuit 104, and a binary counter 105.

Signal conditioning circuits 101 comprise seven conventional voltage follower circuits which have an output voltage that follows the input voltage. Each of the signal conditioning circuits 101 receives the instantaneous signal from one of the seven sensors and generates an amplified, filtered signal at its output. By isolation of each sensor signal from the load at multiplexer circuit 102, signal conditioning circuits 101 prevent undesired interactions or "loading" effects between the sensors and the load.

Multiplexer 102 converts a number of parallel input voltages into a serial string of those voltages. Of the signals on the input channels of multiplexer 102, seven are the instantaneous signals from the seven signal conditioning circuits 101 and one is a reference signal. The signal on the output channel of multiplexer 102 is the instantaneous input signals encoded into the amplitude of a train of finite-width pulses as shown in the PAM signal of FIG. 4.

Voltage-to-pulse width circuit 103 is coupled to the output of the multiplexer 102. The circuit encodes the information contained in the amplitude of the output signal from multiplexer 102 into a variation in the duty cycle of the pulses from circuit 103. Thus, the higher the amplitude of the signal from multiplexer 102, the longer the output pulse from circuit 103 will remain in the high state.

Binary counter circuit 105 provides the time divisions for multiplexer 102. As configured, counter circuit 105 provides $2^3$ or 8 time divisions in which to modulate the input signals. In this manner, one of the seven independent signal conditioning circuits 101 and the reference signal is sampled by multiplexer 102 at one of the eight different time divisions clocked by counter 105.

The counter 105 is clocked by the output signal from the voltage-to-pulse width circuit 103. Clocking occurs whenever the voltage state of this signal changes from logic low to logic high which in turn occurs at a predetermined frequency.

Radio transmitting circuit 104 can be any conventional radio transmitting circuit. Components of a conventional radio transmitting circuit typically include a radio frequency oscillator, and a final power output stage. The input terminal of radio transmitting circuit 104 receives the output signal from the pulse-duration modulating circuit 103. In response to this input signal, the radio transmitting circuit 104 generates radio carrier frequency signal bursts having a duration determined by the duty cycle of the signal from circuit 104. The carrier frequency can be set at any desired frequency in the radio frequency spectrum. Relatively high frequencies are preferred because this reduces the power requirements of the telemetry circuit and therefore the size of the components of the circuit. Smaller components in turn facilitate the mounting of these components to the Hawley appliance. As configured in the preferred embodiment, the radio carrier frequency of circuit 104 is 100 Mhz.

Figures 2, 3, 4, 5:
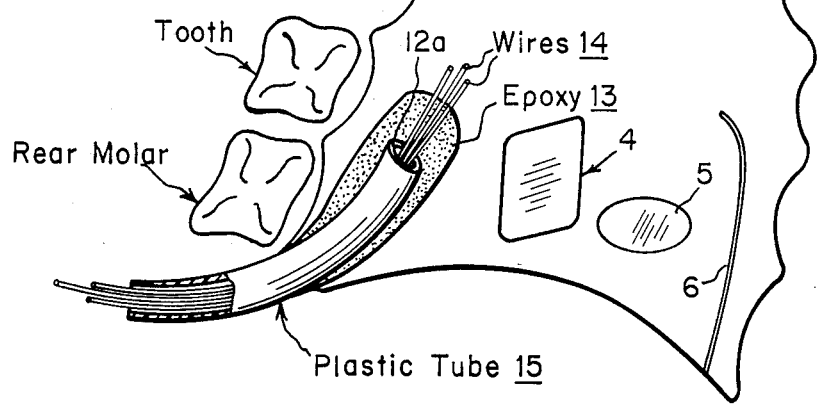
Figure 3:
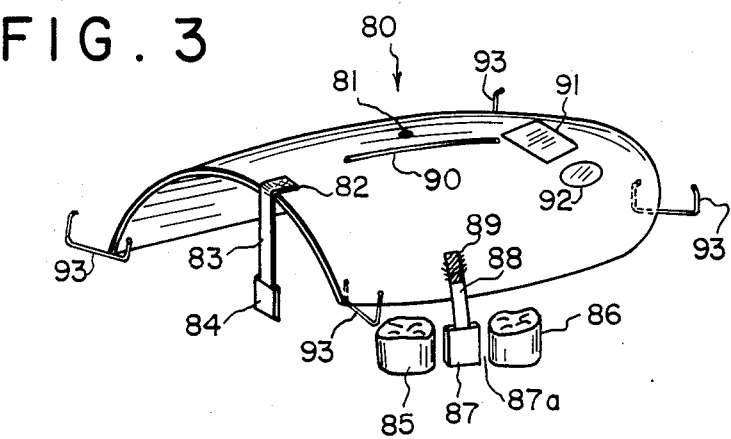
Figure 4:
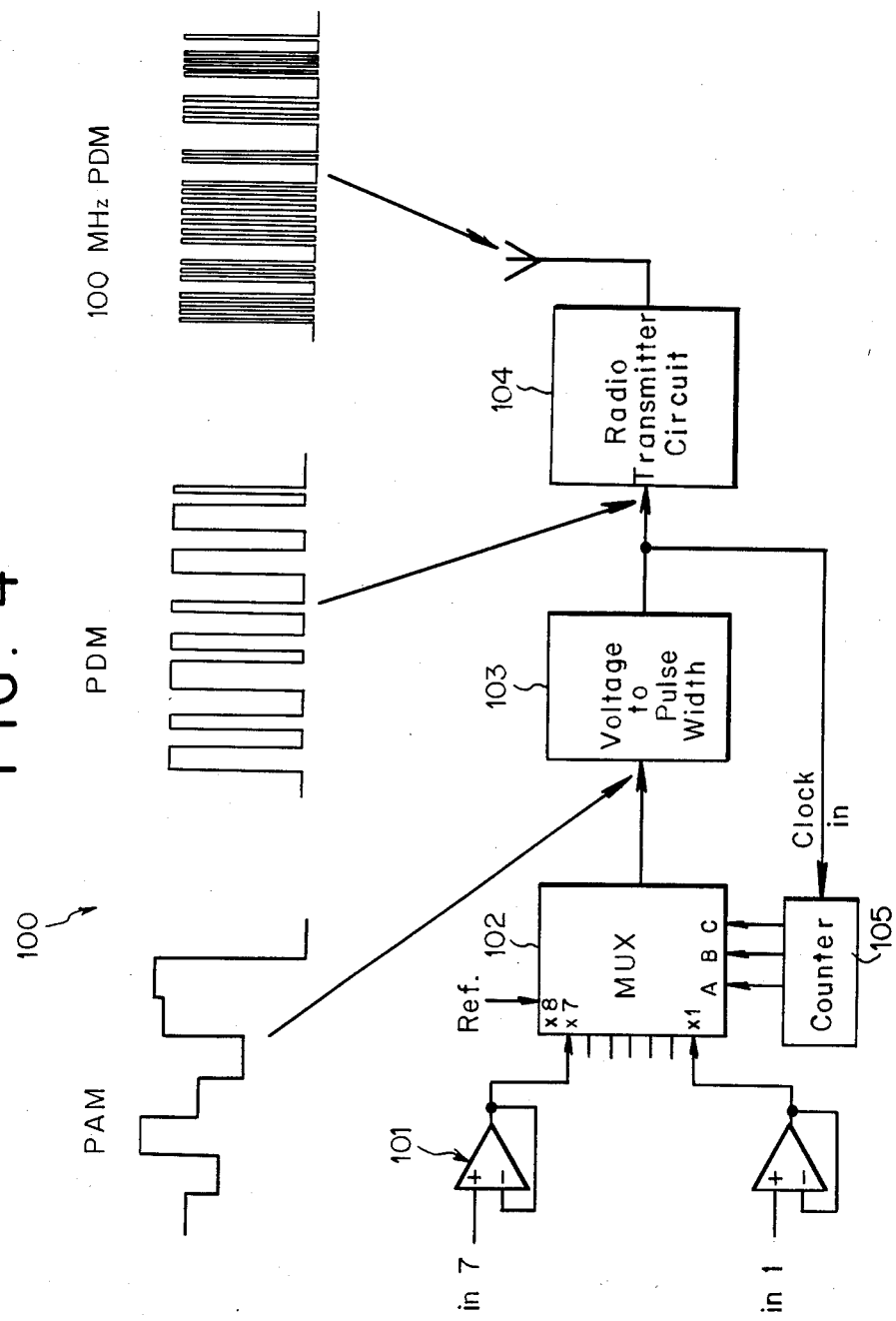
Figure 5:
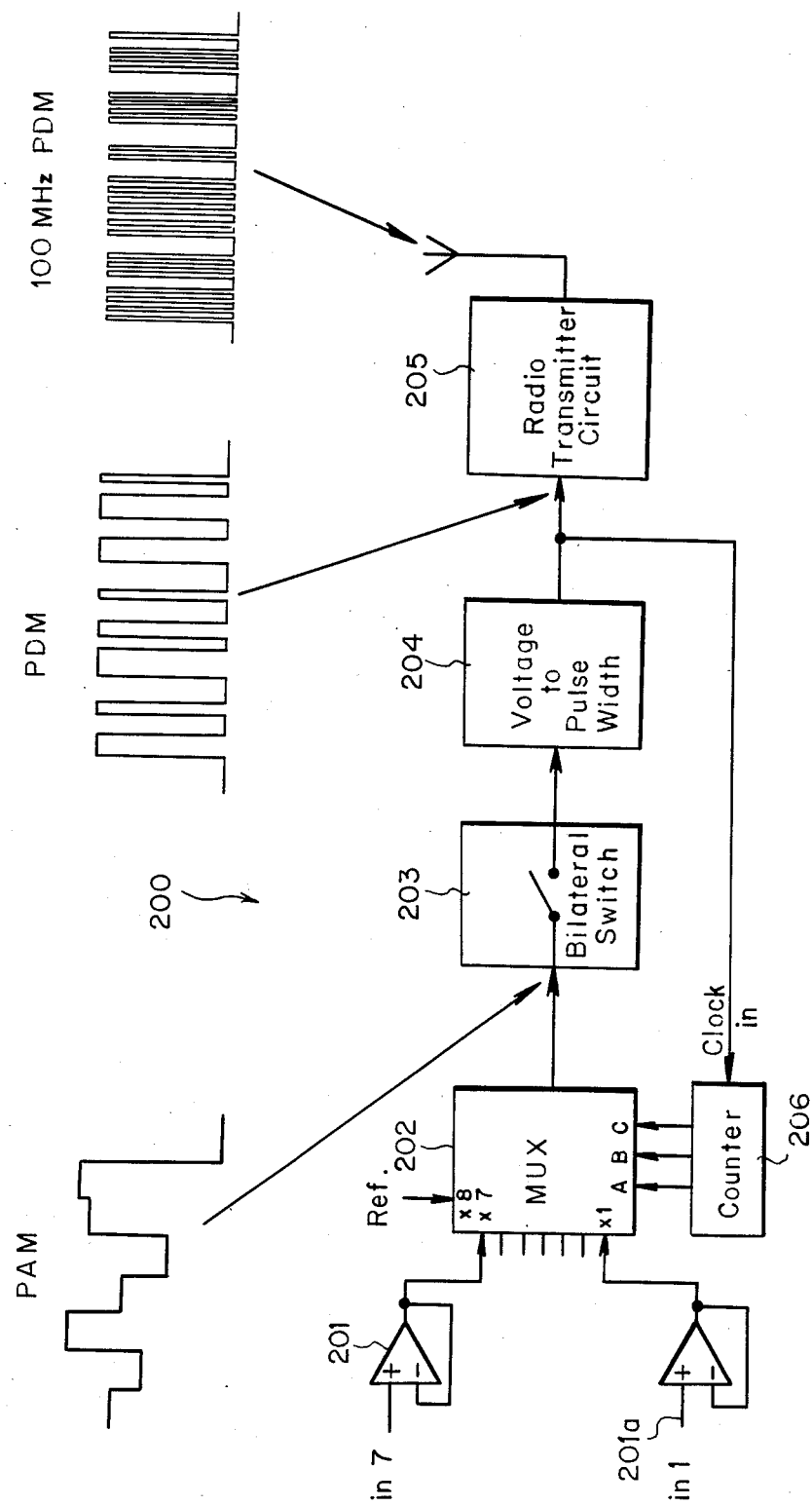

FIG. 5 depicts another preferred embodiment of the telemetric circuit for radio telemetry of intraoral activities to a remote location. Circuit 200 broadly includes signal conditioning circuits 201, multiplexer circuit 202, bilateral switch 203, voltage to pulse width circuit 204, and radio transmitter circuit 205.

Signal conditioning circuits 201, multiplexer circuit 202, voltage to pulse width circuit 204, and radio transmitter circuit 205 are identical in scope and operation to the circuits in FIG. 4 which are identified in that figure as elements 101, 102, 103, and 104, respectively.

Bilateral switch circuit 203 is an electrical signal throw double pole switch. The switch closes whenever it senses a change in voltage state from logic reference to logic high, which occurs whenever circuit 202 starts to sample the signal from sensor 201a. Since this occurs only at the start of each sampling cycle, bilateral switch 203 advantageously assures that the output signal from the switch is synchronized with the input signal to the pulse amplitude modulating circuit 202.

Figure 6:
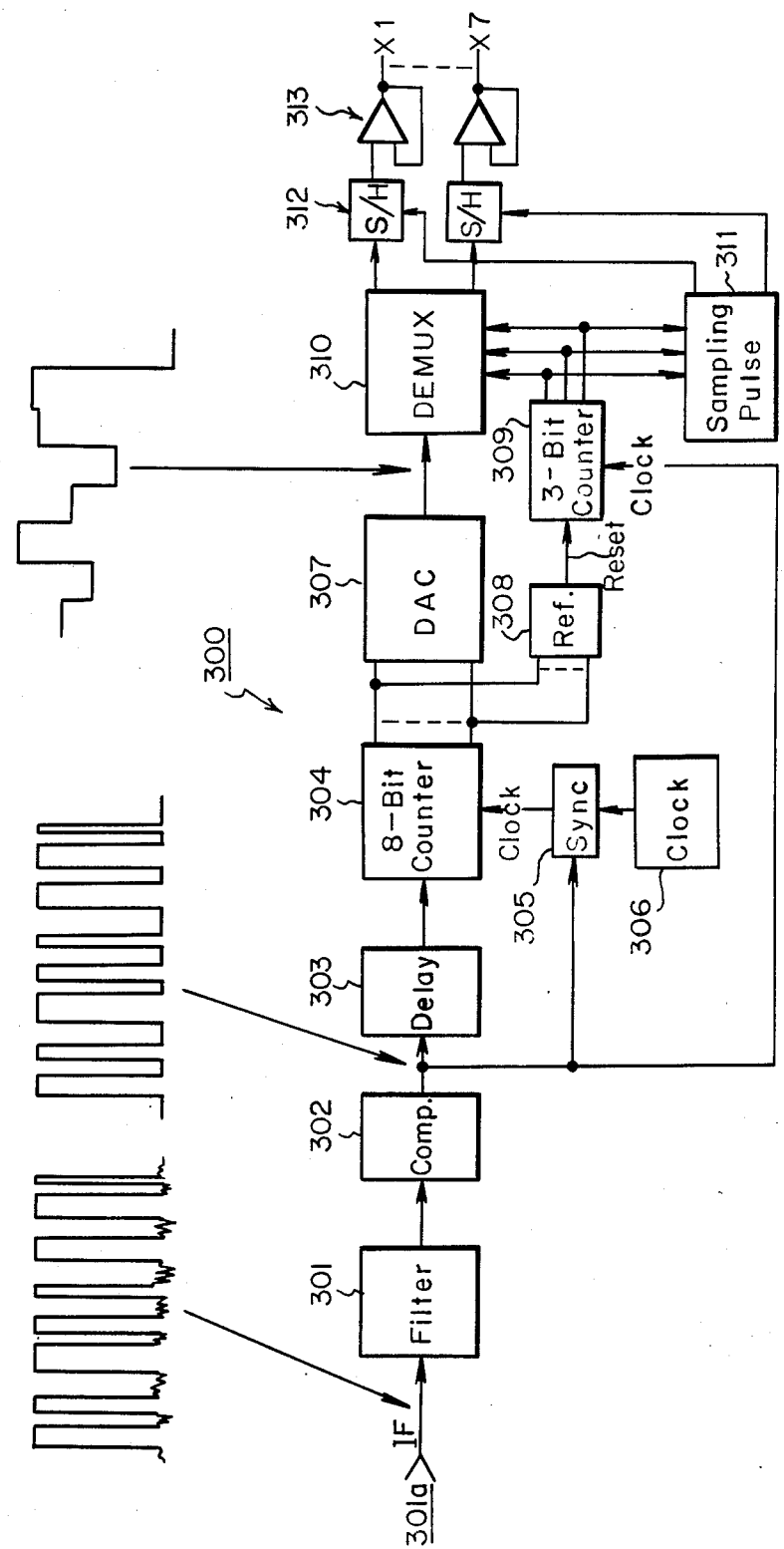
FIG. 6 is a schematic of a remotely located receiver and demodulator circuit for receiving telemetry signals which are broadcast from the telemetry unit attached to the Hawley appliance.

FIG. 6 depicts a preferred embodiment of a remotely located receiver and demodulator circuit 300 which receives the radio signal broadcast from the radio telemetry circuit 100 and demodulates such signal to obtain the intraoral information. Circuit 300 comprises a radio antenna receiver circuit 301a, a filter circuit 301, a comparator circuit 302, a delay circuit 303, an 8-bit counter circuit 304, a digital-to-analog converter circuit 307, a demultiplexer circuit 310, sample and hold circuits 312, and signal conditioning circuits 313.

Radio antenna receiver circuit 301a can be any conventional radio antenna receiver circuit which receives the radio signals which are broadcast from the radio transmitter circuit 104 and recovers the information encoded in them. Components of a conventional radio antenna receiver circuit include an amplifier with tuner to separate a particular channel or frequency from the other frequencies picked up by the antenna. Radio antenna receiver circuit 301a isolates the radio signal which is broadcast from the radio transmitter circuit and outputs this signal to filter circuit 301.

Filter circuit 301 is a band pass filter which is configured to attenuate all but the radio carrier frequency. Filter circuit 301 reduces the amplitude of unwanted harmonics and spurious responses and permits the radio frequency signal with encoded information to pass to comparator circuit 302.

Comparator circuit 302 is a comparator circuit which detects the voltage level of the input signal and converts this voltage level into either a logic low or a logic high voltage state. In this manner, a signal is generated which contains in a pulse duration modulated format the information from the sensors located on the Hawley appliance.

Demodulation of the pulse-width modulated signal which is output from comparator circuit 302 is accomplished in two steps. First, the pulse-width modulated signal is demodulated by the 8-bit counter 304 and the digital-to-analog converter circuit 307 into a pulse-amplitude modulated signal. Second, the pulse-amplitude modulated signal is further demodulated by the demultiplexer circuit 310 into signals which correspond to the information from the sensors located on the Hawley appliance.

Demodulation of the pulse-width modulated signal at the output of comparator circuit 302 is accomplished on a pulse-to-pulse basis by using 8-bit counter circuit 304, clock circuit 306, synchronization circuit 305, delay circuit 303 and digital-to-analog converter 307 to determine the length of the duty cycle of each pulse.

The 8-bit counter circuit 304 is a divide-by-8 ripple counter that ripple counts in the binary-up direction. The pulse-width modulated signal at the output terminal of the comparator circuit 302, which is time-delayed by delay circuit 303, sets this 8-bit counter circuit 304 into the count mode of operation. This occurs whenever the voltage state of the pulse-width modulated signal changes from a logic low state to a logic high state. Once in the count mode of operation, the clock signal from clock circuit 306, which is time synchronized with the pulse width modulated signal by synchronization circuit 305, clocks the 8-bit counter circuit 304 in the binary-up direction to generate ripple counts on the eight output terminals of that counter. The counter circuit stops counting whenever the voltage state of the pulse-width modulated signal changes from a logic high state to a logic low state. When this occurs, the digital count on the 8-output terminals of the counter circuit is a measure of the duty cycle of the pulse duration modulated signal and therefore represents the information contained in that pulse.

Delay circuit 303 is a delay circuit for introducing a predetermined time lag into an incoming signal. Delay circuit 303 receives the instantaneous signal from the comparator circuit 302 and delays this signal by a predetermined time period. This time period permits the signal to set 8-bit counter circuit 304 into the count mode of operation only after the clock signal from clock 306 becomes synchronized with that signal.

Clock circuit 306 is a clock circuit which generates square wave signals at a rate such that the count capacity of counter 304 is not exceeded by a pulse signal of maximum duty cycle.

Synchronization circuit 305 is a switching circuit which performs the logic "AND" operation. Only when the pulse-width modulated signal from comparator circuit 302 is in a logic high voltage state does the synchronization circuit 305 permit the clock signal from clock circuit 306 to clock the 8-bit counter circuit 304.

In this manner, synchronization circuit 305 switches on and off bursts of clock counts to 8-bit counter circuit 304 in accordance with the logic high and logic low voltage state of the pulse-width modulated signal.

Digital-to-analog converter circuit 307 decodes the digital counts on the output terminals of the 8-bit counter circuit 304. This circuit changes these digital counts into an analog signal. The circuit is configured to sample at predetermined time intervals (i.e., once for each time division) the digital counts on the output terminals of the 8-bit counter circuit 304. The output signal of this circuit is a signal comprising a train of pulses having a predetermined pulse-width and having an amplitude which is determined by the number of digital counts sampled. In this manner, a signal is generated which contains in a pulse amplitude modulated format the information from the sensors located on the Hawley appliance.

Demodulation of the pulse-amplitude modulated signal which is output from the digital-to-analog converter 307 is accomplished by demultiplexer circuit 310, reference circuit 308, 3-bit counter circuit 309, sample-and-hold circuits 312, sampling pulse circuit 311, and signal conditioning circuits 313.

Demultiplexer circuit 310 is a 3-to-8 decoder/demultiplexer circuit which demodulates one carrier into eight signals of information. The signal on the input channel of the demultiplexer circuit 310 is the pulse amplitude modulated signal from the digital to analog circuit 307. Each signal on the 8-output terminals of the demultiplexer circuit 310 corresponds to the signal generated by one of the seven sensors in the Hawley device or the reference signal of multiplexer 102 in FIG. 4.

Selection of one of the eight output terminals of circuit 307 is by 3-bit counter circuit 309 which is a 3-bit binary ripple counter that ripple counts in the binary up direction. The 3 bits of this counter permit selection of $2^3$ or the 8 output terminals of demultiplexer circuit 309.

The clock input to 3-bit counter 309 is the pulse-width modulated signal from comparator circuit 302. Clocking occurs whenever the voltage state of this signal changes from a logic low state to a logic high state.

Reference circuit 308 resets the 3-bit counter 309. The circuit receives the digital counts from 8-bit counter circuit 304 and generates a signal having a logic low voltage state whenever this digital count equates to a predetermined number which has been previously digitally programmed into the reference circuit 308. Because the reference circuit 308 is electrically coupled to the reset terminal of the 3-bit counter 309, every logic low voltage state signal from reference circuit 308 resets the 3-bit counter 309 to the zero reference state. In this manner, counter 309 begins another series of eight counts.

Each of the eight sample-and-hold circuits 312 samples an input signal and stores this signal as an analog voltage accurately over a time range. The eight output terminals of the demultiplexer circuit 310 are electrically coupled to the eight sample-and-hold circuits 312 to form a hardware handshaking bus. This hardware handshaking bus is sampled by circuits 312 at a predetermined frequency which is determined by the sampling pulse circuit 311. The circuits 312 output these sampled voltages until the next sampling period permits these circuits to update these output signals.

Sampling pulse circuit 311 is a 3-to-8 decoder which activates one of the eight sample-and-hold circuits according to the 3-bit digital code which is input to this circuit by counter 309. As a result, sampling pulse circuit 311 clocks each sample-and-hold circuit at a different time so that the sampling of each signal on the wires of the handshaking bus occurs at a different time. Signal conditioning circuits 313 are identical in scope and operation to the signal conditioning circuits 101 in FIG. 4. Signal conditioning circuits 313 receive the signal from the sample-and-hold circuits 312 and generate an amplified, filtered signal at each output. By isolation of the sample-and-hold circuits 312 from the loads placed on the output of the conditioning circuits, the signal conditioning circuits prevent any undesired interactions or "loading" effects between circuits 312 and the loads.

Figure 7:
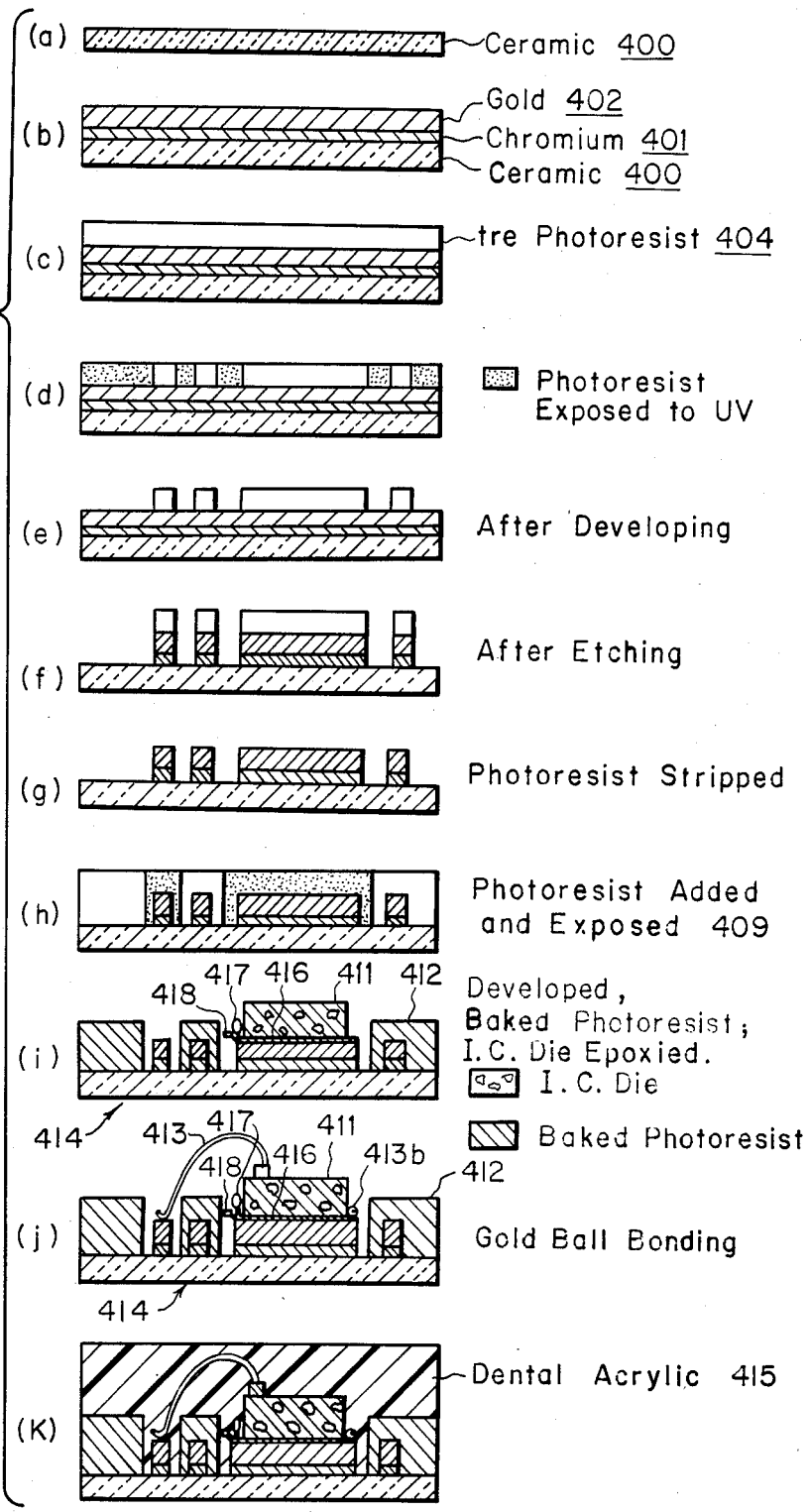
FIG. 7 is an illustrative seven channel telemetry circuit fabricated in accordance with this invention for radio telemetry of the electrical signals from the sensors which are attached to the Hawley appliance.

The flow chart and cross-sectional profiles of FIG. 7 depict a method for fabricating as a thin film hybrid micro-circuit a seven channel telemetry circuit for radio telemetry of electric signals from seven intraoral sensing devices. As indicated therein a starting substrate 400 is a 5 cm×5 cm×⅓ mm ceramic wafer. A chromium layer 401 is evaporated onto the substrate to a depth of 200 Å in order to improve the adhesive properties of a subsequent layer of gold to the substrate. A gold layer 402 is then evaporated onto this substrate to a depth of 5000 Å. Next, a negative-acting photoresist layer 404 is placed on the gold layer 402. The photoresist layer is selectively exposed through a mask (not shown) to ultraviolet light to define a desired conducting line and bonding pad layout for the seven channel telemetry circuit. After developing and removing the unexposed portions of the photoresist, the underlying exposed portions of gold layer 402 are etched with a gold etchant as shown in FIG. 7(e) and 7(f). The photoresist material is then stripped off the gold layer as shown in FIG. 7(g) leaving on the surface of substrate gold conducting lines having a width of about 100 micrometers and bonding pads.

To fabricate an insulating layer over the conducting lines, a layer 409 of Shipley positive-acting photoresist is placed on the substrate and is exposed through a mask (not shown) to ultraviolet light to define the desired insulator pattern as shown in FIG. 7(h). After developing and removing the exposed portions of the photoresist, the underlying unexposed portions of the photoresist are baked at about 150° C. for 30 minutes as shown in FIG. 7(i). The purpose of the baking is to improve the bonding properties between the photoresist and the substrate. As a result of the baked photoresist layer 412, all but the telemetry circuit bonding pads are electrically insulated by the non-conducting photoresist as shown in FIG. 7(i). Integrated chips 411 containing the telemetry circuit are epoxied onto a grounded pagd 416 which is epoxy mounted on the substrate 414. Chip capacitors 417 and chip resistors 418 are attached to the substrate using electrically conducting silver epoxy. The integrated chips 411 are then connected to the substrate using gold-ball bonding 413. Enamel shrouded wire 413b is then epoxied onto the bonding pads 416 for external connections such as power supply and input and output terminals. Finally, the entire thin film hybrid micro-circuit 414 is covered with epoxy and then dental acrylic 415 to electrically insulate the circuit and to prevent moisture from migrating into the circuit.

What is claimed is:

1. A dental assembly useful for the measurement of parametric changes throughout the oral cavity comprising:

a Hawley appliance;

a sensor assembly mounted on said Hawley appliance comprising one or more sensors having means for measuring parametric changes throughout the oral cavity and which provide an electrical output signal in response to said changes in one or more of the intraoral parameters;

a lead to each sensor;

means mounted on said Hawley appliance for transmitting said electrical output signal from the oral cavity using only a modulated radio frequency carrier; and means for hermetically sealing said sensor assembly, said lead and said transmitting means.

2. The dental assembly of claim 1 wherein said transmitting means comprises:

a telemetry transmitter circuit mounted on said Hawley appliance for telemetry of signals from said intraoral sensor comprising:

signal conditioning means coupled to said sensor and responsive to its electrical output signal for producing signal amplification and filtering;

modulating means coupled to said signal conditioning means and responsive to its electrical output for encoding that signal output for telemetry transmission; and transmitting means coupled to said modulating means and responsive thereto for generating an output signal representative of the signals from said antenna transmitter device mounted on said Hawley appliance comprising an antenna element coupled to said telemetry circuit and responsive to the output signal of said circuit for broadcasting said signal to a remote location; and a power pack assembly mounted on said Hawley appliance comprising a power pack element which provides electric energy to said telemetry transmission circuit and said sensor assembly.

3. The dental assembly of claim 1 wherein at least one sensor is a pH sensitive sputtered iridium oxide electrode for intraoral pH monitoring.

4. The dental assembly of claim 1 wherein at least one sensor is a pressure sensitive PV2 piezoelectric polymer sensor for intraoral chew event monitoring.

5. The dental assembly of claim 1 wherein at least one sensor is a pressure sensitive PV2 piezoelectric polymer sensor for intraoral swallow event monitoring.

6. The dental assembly of claim 1 wherein the telemetry transmitter circuit includes a switching means coupled to the modulating means and wherein the switching means is responsive to an output signal of said modulation means for synchronizing said signal with the input signal to the modulating means.

7. The dental assembly of claim 1 further comprising a remotely located receiver and demodulator circuit for receiving said broadcast signal and demodulating the same to obtain converted intraoral information.

8. The dental assembly of claim 1 wherein at least one sensor is a pressure sensitive PV2 piezoelectric polymer sensor for intraoral chew event monitoring that is located on an open bite location of the mouth where the maxillary and mandibula are not in contact when the mouth is closed and is held in place by a cantilever mounted on the Hawley appliance and terminating at the open bite location.

9. The dental assembly of claim 1 wherein at least one sensor is a pressure sensitive PV2 piezolelectric polymer sensor for intraoral swallow event monitoring wherein the sensor is located near the uvula and is held in place by a cantilever mounted on the Hawley appliance and terminating at the uvula location.

10. A method for modifying a Hawley appliance to mount a sensor and a telemetry unit for measurement of parametric changes throughout the oral cavity comprising the steps of:
   attaching a sensor having means for measuring parametric changes throughout the oral cavity to the Hawley appliance so as to measure one or more of said parametric changes;
   forming channels on the lingual side of said appliance for a radio telemetry unit, a power pack, an antenna, and wire interconnection placements;
   interconnecting said sensors, telemetry unit, antenna, power pack by wires into a discrete package;
   attaching telemetry unit, antenna, power pack and wire connections to the Hawley appliance; and
   sealing all sensors, telemetry unit, antenna, power pack and wire conncetions against moisture migration.

11. The method of claim 10 comprising the additional steps of:
   molding thicker acrylic on the lingual side of said appliance for interproximal sensor placement;
   forming holes between the lingual side and interproximal side of said appliance to accommodate the sensors;
   drilling holes between the lingual side and soft palate side of said appliance to permit fit of at least one reference sensor; and
   positioning said sensors in said holes with sensors oriented toward intraoral activity to be monitored.

12. The method of claim 10 comprising the additional step of mounting one end of a cantilever onto the lingual side of the Hawley appliance with a sensor fixedly attached to the other end of said cantilever.

13. A method for remote monitoring of parametric changes throughout the oral cavity comprising the steps of
   monitoring said parametric changes by one or more sensors having means for measuring parametric changes throughout the oral cavity and being mounted on a Hawley appliance within a patient's mouth and capable of generating a signal proportional to the instantaneously measured parametric changes;
   converting said monitored signals to proportional amplified and filtered signals;
   modulating said signals for radio telemetry transmission;
   broadcasting said modulated signal from the patient's mouth upon a radio frequency carrier; and
   receiving and demodulating said broadcast signal to obtain a signal whose waveform is similar to the electrical signals form the intraoral sensors.

14. A method for fabricating a thin film hybrid micro-circuit for telemetry of electric signals from intraoral sensing devices comprising the steps of:
   depositing a chromium layer on the substrate;
   depositing a gold layer on the substrate;
   placing a first layer of negative-acting photoresist on the substrate;
   placing a first mask containing a negative impression of the telemetry conducting line and bonding pad layout on the substrate;
   exposing the photoresist layer through the mask to ultraviolet light;
   removing the first mask;
   developing and removing the unexposed portions of the photoresist;
   etching the gold layer with a gold etchant;
   removing the exposed photoresist, leaving bare the surface of the substrate except for the gold region covered by the conducting line and bonding pad
   placing a second layer of positive-acting photoresist on the substrate;
   placing a second mask containing a positive impression of the telemetry circuit conducting line layout on the substrate;
   exposing the photoresist layer through the mask to ultraviolet light;
   developing and removing the exposed portions of the photoresist;
   baking the photoresist mask;
   expoxying an integrated circuit with the telemetry circuit onto grounding pads epoxied to the substrate;
   mounting at least one capacitor or resistor on the substrate;
   connecting the integrated circuit to the substrate;
   mounting at least one insulated wire onto the bonding pads for an external connection; and
   covering the entire thin film hybrid micro-circuit with dental acrylic.

15. A dental assembly useful for the measurement of chemical or ionic species throughout the oral cavity comprising:
   a Hawley appliance;
   a sensor assembly having means for measuring parametric changes throughout the oral cavity and being mounted on said Hawley appliance comprising one or more electrochemical sensors and a reference electrode, said electrochemical sensors providing an electrical output signal in response to changes in one or more chemical or ionic properties;
   a lead to each sensor and reference electrode;
   means mounted on said Hawley appliance for transmitting said electrical output signal from the oral cavity using only a modulated radio frequency carrier; and
   means for hermetically sealing said sensor assembly, said lead and said transmitting means.

16. The dental assembly of claim 15 wherein at least one sensor is a pH sensitive electrode for intraoral pH monitoring.

* * * * *